United States Patent
Gendimenico et al.

(10) Patent No.: US 6,488,940 B2
(45) Date of Patent: *Dec. 3, 2002

(54) USE OF 17-α-ESTRADIOL FOR THE TREATMENT OF AGED OR SUNDAMAGED SKIN AND/OR SKIN ATROPHY

(75) Inventors: Gerard J. Gendimenico, Neshanic Station, NJ (US); James A. Mezick, East Brunswick, NJ (US)

(73) Assignee: Johnson & Johnson Consumer Companies, Inc., Skillman, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/131,549

(22) Filed: Aug. 10, 1998

(65) Prior Publication Data

US 2001/0051167 A1 Dec. 13, 2001

Related U.S. Application Data

(63) Continuation-in-part of application No. 09/129,645, filed on Aug. 5, 1998.
(60) Provisional application No. 60/056,485, filed on Aug. 21, 1997.

(51) Int. Cl.$^7$ ............................ A61K 7/00; A61K 7/42; A61K 7/48
(52) U.S. Cl. ........................................ 424/401; 424/59
(58) Field of Search .................................. 424/401, 59

(56) References Cited

U.S. PATENT DOCUMENTS

| 4,390,532 A | * | 6/1983 | Stuttgen et al. | |
| 4,855,322 A | * | 8/1989 | Kasha et al. | |
| 5,461,064 A | * | 10/1995 | Cullinan | |
| 5,656,286 A | | 8/1997 | Miranda | 424/449 |
| 5,849,312 A | | 12/1998 | Breton et al. | |
| 5,932,229 A | | 8/1999 | Ptchelintsev et al. | 424/401 |

FOREIGN PATENT DOCUMENTS

| EP | 0 765 663 | 4/1997 | ......... A61K/31/565 |
| WO | WO 87/07138 | 12/1987 | ........... A61F/13/00 |

OTHER PUBLICATIONS

PCT Search Report dated Jan. 29, 1999 for corresponding PCT Appln. No. PCT/US98/17046.

Lorraine H. Kligman, "Animal Models of Photodamage and Its Treatment", in *Photodamage,* Barbara A. Gilchrest, MD, p. 137–153 (1995).

"The Effect of Oestrogenic Treatment on the Acid Mucopolysaccharide Pattern in Skin of Mice", Nina Grossman et al.; Acta Phamacol. et toxicol, 1971, 30, pp. 458–464.

XP–002089138 Steroids in Dermatology and Cosmetics vol. 36, 1963 pp. 1097–1103 Dec. 1963.

XP—002089139 File Chemical Abstracts, vol. 85, AN=166579 Dec. 1976.

XP–002089140 File Medline, AN=76177467 Apr. 1976.

XP–002089141 File Medline AN=80246878 Dec. 1980.

* cited by examiner

Primary Examiner—Thurman K. Page
Assistant Examiner—Amy Pulliam

(57) ABSTRACT

The present invention relates to a method for treatment of mammalian skin conditions where stimulated connective tissue synthesis is beneficial, comprising treating skin in need of such treatment with a safe and effective amount of 17-α-estradiol.

8 Claims, No Drawings

USE OF 17-α-ESTRADIOL FOR THE TREATMENT OF AGED OR SUNDAMAGED SKIN AND/OR SKIN ATROPHY

CROSS REFERENCE TO RELATED APPLICATION

This is a continuation-in-part of patent application Ser. No. 09/129,645, filed Aug. 5, 1998, and hereby incorporates by reference all subject matter disclosed therein. This also claims the priority of Provisional Application No. 60/056,485, filed Aug. 21, 1997.

FIELD OF THE INVENTION

The present invention relates to a method of treating mammalian skin conditions to stimulate connective tissue synthesis in situations in which such connective tissue synthesis is beneficial. Specifically, the invention relates to novel compositions and methods of using the composition for treatment of aged skin, sun-damaged skin, acne, skin atrophy and for healing of wounds.

BACKGROUND OF THE INVENTION

Estrogens are hormonal compounds that exert wide-ranging biological effects on target tissues. The major organs affected by estrogens are the reproductive tract, genitals, bone, blood vessels and skin.

The most important natural estrogen is 17-β-estradiol, considered the hormone responsible for most, if not all the normal physiologic processes of this class of compounds. Two other natural estrogens are estrone, a precursor of 17-β-estradiol and estriol, a metabolic product of 17-β-estradiol.

Another estrogen, 17-α-estradiol, is the isomer or epimer of 17-β-estradiol and is biologically much weaker than its β-isomer when given systemically. In animal studies, 17-α-estradiol is reported to possess only 0.4 to 2% of the potency of 17-β-estradiol on reproductive function in rodents. When administered to humans subcutaneously, 17-α-estradiol lacked biological activity on a number of markers of reproductive function. For these reasons, 17-α-estradiol is thought to be a physiologically unimportant estrogen and, accordingly, to have minimal therapeutic value or medicinal use.

The skin is known to respond to some estrogens including 17-β-estradiol. Estrogens stimulate fibroblasts within the dermis and increase the levels of connective tissue matrix molecules. The synthesis of collagen, elastin and non-protein molecules such as hyaluronic acid are elevated when estrogens are administered by systemic or topical routes. Consequently, skin maintains or has an enhanced thickness and integrity. Such skin has a better appearance and is functionally able to resist environmental stresses. Topical treatment of the skin of estrogen-deficient women also showed effacement of wrinkles, increase in water content and improved skin elasticity when treated topically with 17-β-estradiol. In addition, when wounded, skin would be expected to heal more rapidly in the presence of estrogens because fibroblasts would be in an activated state.

Because 17-β-estradiol affects multiple organ systems, it is not desirable to use this chemical in treatment solely of topical skin-related conditions. Rather, it would be more desirable to use an estrogen that is more selective in its action on skin. Although 17-β-estradiol can be administered topically and have local effects on skin, it has the potential to be absorbed into the bloodstream where it can cause undesirable biological responses in non-cutaneous tissues. For example, the delivery of 17-β-estradiol for estrogen replacement therapy is commonly accomplished through sustained release from a device that is applied topically to skin. This method of delivery demonstrates that 17-β-estradiol is ideally suited as a compound to cross the skin barrier and accumulate in the bloodstream. Thus by this route, sufficient blood levels of 17-β-estradiol can be achieved to exert biological activity on all organ systems. Thus, topical administration of 17-β-estradiol is undesirable, although its effects may be beneficial to the skin.

Surprisingly, we have discovered that a relatively unimportant entity which has low potency in biological systems, 17-α-estradiol, may be used as a topical treatment that is more selective in its effects on skin. Our studies show that topical 17-α-estradiol is just as effective as 17-β-estradiol at inducing the synthesis of new connective tissue molecules in the dermis of mouse skin, yet, because of its weak activity as a systemically administered estrogen, 17-α-estradiol is expected to exert insignificant biological responses on non-cutaneous tissues such as the reproductive tract if it is absorbed into the bloodstream after topical application. While the use of 17-α-estradiol has been reported in connection with alopecia, hair loss or hair growth, there has been no data showing that it was effective in the treatment of other skin conditions.

Thus it is an object of our invention to provide a method for treatment of skin conditions where stimulated connective tissue synthesis is beneficial.

It is yet another object of this invention to provide a method for treatment of skin conditions including aged, sun-damaged skin, skin atrophy and for healing of wounds, without undue side effects.

It is yet another object of the invention to provide a novel composition containing a pharmaceutically effective agent and a pharmaceutically acceptable carrier for use in treating skin in which synthesis of connective tissue is beneficial.

SUMMARY OF THE INVENTION

We have found, surprisingly, that a composition containing a connective tissue synthesizing-effective amount of 17-α-estradiol and a pharmaceutically acceptable carrier can be used in a method of treating the skin which would benefit from connective tissue synthesis by topical application. Unexpectedly, the compositions of this invention are capable of generating connective tissue synthesis when applied topically, but do not engender other biological or physiological effects systemically. Furthermore, we have also found that an epidermal proliferation enhancing-effective amount of 17-α-estradiol and a pharmaceutically acceptable carrier can be used in a method of treating the skin which would benefit from enhanced epidermal proliferation, such as in the treatment of acne and other such skin conditions.

DETAILED DESCRIPTION OF PREFERRED EMBODIMENTS

The compositions and methods of this invention relate to the use of 17-α-estradiol as a topical treatment of skin which requires the stimulation of connective tissue synthesis, such as skin which is aged or sun-damaged and/or enhancement of epidermal proliferation, such as skin which is affected by acne or other conditions.

More particularly, this invention relates to novel compositions and methods of using the composition for treatment of aged, sun-damaged skin, skin atrophy, acne and for healing of wounds and possibly for prevention of scarring due to trauma to the skin, inter alia. The estrogen 17-α-estradiol is a compound of the following structure:

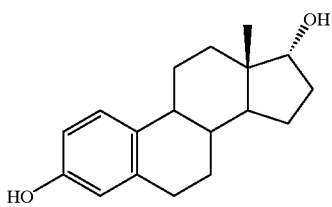

Compositions of the present invention preferably contain 17-α-estradiol in an effective amount to stimulate connective tissue synthesis and/or enhance epidermal proliferation and/or generally affect skin-related growth processes. Preferably, the compositions of this invention contain from about 0.001% to about 5%, more preferably from about 0.01% to about 2% and most preferably from about 0.1% to about 1% by weight of the active ingredient, 17-α-estradiol.

The compounds which are active in the compositions and methods of this invention may be delivered topically by any means known to those of skill in the art. If the delivery parameters of the topically active pharmaceutical or cosmetic agent so require, the topically active composition of this invention may preferably be further composed of a pharmaceutically or cosmetically acceptable vehicle capable of functioning as a delivery system to enable the penetration of the topically active agent into the skin. Thus, the topically active composition of this invention may be formulated in the form of a liquid, gel or cream or any other conventional pharmaceutically or cosmetically acceptable vehicle.

Preferably, the compositions of this invention are applied to the skin over a period of time sufficient to affect skin-related processes, e.g., stimulate connective tissue synthesis or enhance epidermal proliferation. Generally, the effects of the application and use of the compositions of this invention become visible after approximately four to about twenty-four weeks of treatment. It is preferable to apply the compositions of this invention in an effective amount once or twice per day. The compositions of this invention may also be administered orally The compositions of this invention may contain, in addition to 17-α-estradiol, other dermatologically active compounds and materials. For example, sunscreen ingredients, alpha hydroxy acids, retinoids, beta hydroxy acids, antiinflammatories, antibacterials, antifungals, antioxidants and other active ingredients may be combined with 17-α-estradiol to treat and/or prevent particular dermatological conditions such as erythema, acne, photodamage, psoriasis and others known to those of ordinary skill in the art.

The compositions of this invention may be formulated as creams, oils, gels, emulsions, ointments or other forms known to those of ordinary skill in the art.

The stimulatory activity of 17-α-estradiol on connective tissue synthesis in the dermis may be demonstrated by the following two methods. In one method, a deficit in connective tissue synthesis is induced by long-term exposure of mouse skin to ultraviolet (UV) radiation. This model has been used to demonstrate the reparative effects of retinoids on connective tissue synthesis after cessation of UV exposure. The repair can be visualized as a region of new connective tissue which forms as a subepidermal band in the papillary dermis after topical retinoid treatment (Kligman L H, Chapter 10: Animal Models of Photodamage and Its Treatment, pp. 136–156, In: Photodamage, edited by B. A. Gilchrest, 1995, Blackwell Science, Cambridge, Mass.). The old malformed elastotic tissue, produced during UV exposure, is compressed by the retinoid-induced new connective tissue zone.

In the second method, topical estrogens increase the thickness of the entire skin by enhancing its water content. This is due to estrogen-stimulated increases in hyaluronic acid, which is a biomolecule that has an avid water binding capacity (Grosman et al. Acta Pharmacol. Toxicol., 1971, Vol. 30, pp. 458–464).

Connective tissue photodamage was induced in albino hairless mice (Skh-1) (six to eight weeks old) by exposure of dorsal trunk skin to UV from FS40 fluorescent tubes, three days per week (Monday, Wednesday, Friday) for ten weeks. The UV dose started with one minimal erythemal dose (MED) and was increased gradually to 4.5 MEDs by week 5 and then continued at 4.5 MEDs for five more weeks. At the beginning of week 11, mice were treated topically with 0.1 mL test material on the dorsal trunk skin, three times per week (Monday, Wednesday, Friday) for 6 to 10 weeks. At the end of treatment, dorsal skin was excised and placed in 10% buffered formalin. The specimens were embedded, sectioned and stained with Luna's aldehyde fuchsin for elastic fibers. The dermal repair zone, defined as the area from the epidermal-dermal junction to the top of the compressed elastotic material, was quantified by measuring the depth of the zones with an image analyzer.

Estrogen-induced thickening of the skin was assessed in albino hairless mice (Skh-1). The skin is topically treated for 3 days with 0.1 mL test material. The next day after the last dose, double skin-fold thickness is measured with an engineer's vernier calipers.

The following examples serve as illustrations of the compositions of this invention, however, they do not limit the scope of the invention described herein.

EXAMPLE 1

Albino hairless mice were treated for 10 weeks as set forth above and the repair zone depth was measured.

| Treatment | Dose (%) | Repair Zone Depth ($\mu$m) ± SE |
|---|---|---|
| Vehicle | — | 24.9 ± 0.8 |
| 17-α-estradiol | 0.50 | 71.8 ± 3.0 |
| 17-β-estradiol | 0.01 | 57.4 ± 6.1 |
| All-trans-retinoic acid | 0.03 | 72.0 ± 2.6 |

The results show that 17-α-Estradiol at 0.50% stimulates connective tissue repair more than 17-β-Estradiol and equal to all-trans-retinoic acid, the latter being well known for its beneficial effects on aged or sun-damaged skin.

EXAMPLE 2

This example shows the dose response relationships of 17-α-Estradiol when used for 6 to 10 weeks.

| | | Repair Zone Depth ($\mu$m) ± SE | |
|---|---|---|---|
| Treatment | Dose (%) | 6 Weeks | 10 Weeks |
| Vehicle | — | 24.5 ± 1.0 | 25.2 ± 1.7 |
| 17-α-Estradiol | 0.05 | — | 36.8 ± 2.4 |
| 17-α-Estradiol | 0.1 | — | 44.3 ± 2.3 |
| 17-α-Estradiol | 0.5 | 44.6 ± 2.7 | 51.6 ± 3.5 |
| 17-β-Estradiol | 0.1 | 46.3 ± 0.9 | 38.7 ± 2.5 |
| All-trans retinoic acid | 0.03 | 44.5 ± 3.9 | 59.0 ± 2.3 |

The results show a response dependent upon the dose of the compound as well as the effect of treatment time. Again, 17-α-Estradiol is equivalent in its effects on connective tissue repair compared to 17-β-Estradiol and all-trans-retinoic acid after either six or ten weeks of treatment.

EXAMPLE 3

This example compares the effects of 17-α-Estradiol and 17-β-Estradiol at increasing concentrations compared to the effect of all-trans retinoic acid. Treatments were for 10 weeks.

| Treatment | Dose (%) | Repair Zone Depth (μm) ± SE |
|---|---|---|
| Vehicle | — | 28.0 ± 3.1 |
| 17-α-Estradiol | 0.05 | 34.3 ± 3.7 |
| 17-α-Estradiol | 0.01 | 49.4 ± 3.7 |
| 17-α-Estradiol | 0.5 | 62.4 ± 4.2 |
| 17-β-Estradiol | 0.005 | 45.2 ± 3.1 |
| 17-β-Estradiol | 0.01 | 53.4 ± 2.1 |
| 17-β-Estradiol | 0.1 | 68.2 ± 6.0 |
| All-trans-retinoic acid | 0.03 | 72.0 ± 3.3 |

This shows a dose dependent response of 17-α-Estradiol and 17-β-Estradiol. While 17-β-Estradiol is more potent, 17-α-Estradiol also shows identical therapeutic effect.

EXAMPLE 4

This example compares the effects of 17-α-Estradiol and 17-β-Estradiol on skin thickening after 3 days of topical treatment.

| Treatment | Dose (%) | Skin-Fold Thickness (μm) ± SE |
|---|---|---|
| Vehicle | — | 1.12 ± 0.05 |
| 17-α-Estradiol | 0.01 | 1.16 ± 0.07 |
| 17-α-Estradiol | 0.1 | 1.43 ± 0.06 |
| 17-α-Estradiol | 0.5 | 1.52 ± 0.14 |
| 17-β-Estradiol | 0.001 | 1.25 ± 0.08 |
| 17-β-Estradiol | 0.01 | 1.62 ± 0.11 |
| 17-β-Estradiol | 0.1 | 1.50 ± 0.13 |

This demonstrates that 17-α-Estradiol is as effective as 17-β-Estradiol in its effects on skin thickening due to water retention mediated by increased amounts of hyaluronic acid.

All of these examples show the unexpected topical activity of 17-α-Estradiol on skin connective tissue. Furthermore, since 17-α-Estradiol does not show other estrogenic responses, it has none of the disadvantages of other known estrogens such as 17-β-Estradiol.

EXAMPLE 5

This example shows the dose response relationships of 17-α-Estradiol on thickness of the epidermis when used for 10 weeks.

| Treatment | Dose (%) | Epidermal Thickness (μm) ± SE |
|---|---|---|
| Vehicle | — | 26.6 ± 1.9 |
| 17-α-Estradiol | 0.05 | 29.3 ± 0.3 |
| 17-α-Estradiol | 0.1 | 37.3 ± 1.8 |
| 17-α-Estradiol | 0.5 | 42.9 ± 3.8 |
| 17-β-Estradiol | 0.005 | 32.0 ± 1.2 |
| 17-β-Estradiol | 0.01 | 28.3 ± 1.8 |
| 17-β-Estradiol | 0.1 | 48.1 ± 2.9 |
| All-trans-retinoic acid | 0.03 | 52.8 ± 3.6 |

These results show that 17-α-Estradiol and 17-β-Estradiol act like the retinoid, all-trans-retinoic acid by increasing the thickness of the epidermis. Thus 17-α-Estradiol would be beneficial for skin conditions where the epidermis is atrophied, either due to intrinsic aging of the skin or in pathological conditions caused by excessive sun exposure, wounding, etc. Enhanced epidermal proliferation would also be of value in conditions like acne where stimulation of the follicular epithelia would have a comedolytic effect aiding the expulsion of hyperkeratinized material.

What is claimed is:

1. A method of treatment of mammalian skin conditions, wherein said skin conditions are selected from the group consisting of aged skin, sun-damaged skin, skin atrophy, acne and wound healing, comprising treating skin in need of such treatment with a safe and effective amount of a composition comprising;

a) a safe and effective amount of an active ingredient effective to treat aged skin, sundamagd skin, skin atrophy, acne and wound healing consisting essentially of 17-α-estradiol; and b) a pharmaceutically acceptable carrier.

2. The method of claim 1, wherein the composition comprises from about 0.001% to about 5% of the compound.

3. The method of claim 1, wherein the composition comprises from about 0.05% to about 1% of the compound.

4. The method of claim 1 wherein the pharmaceutically-acceptable carrier is a topical carrier.

5. The method of claim 4, wherein the treatment of the skin with the composition is chronic.

6. The method of claim 5, wherein the treatment of the skin with the composition is for a period of at least 3 months comprising application of the composition from about once a week to about twice a day.

7. A method of treatment of mammalian skin conditions where enhance epidermal proliferation or stimulated connective tissue synthesis is beneficial, comprising treating skin in need of such treatment with a safe and effective amount of a composition comprising:

a) a safe and effective amount of an active ingredient effective to treat aged skin, sun-damaged skin, skin atrophy, acne and wound healing consisting essentially of 17-α-estradiol: and b) a pharmaceutically acceptable carrier.

8. A method of treating mammalian skin conditions which comprises oral administration of a safe and effective amount of a composition comprising:

a) a safe and effective amount of 17-α-estradiol; and b) a pharmaceutically acceptable carrier.

* * * * *

UNITED STATES PATENT AND TRADEMARK OFFICE
CERTIFICATE OF CORRECTION

PATENT NO.    : 6,488,940 B2
DATED         : December 3, 2002
INVENTOR(S)   : Genidimenico et al.

It is certified that error appears in the above-identified patent and that said Letters Patent is hereby corrected as shown below:

Column 5,
Replace lines 25 to 41 with the following:

EXAMPLE 4

This example compares the effects of 17-α-Estradiol and 17-β-Estradiol on skin thickening after 3 days of topical treatment.

| Treatment | Dose (%) | Skin-Fold Thickness [(μm)] (mm) ± SE |
|---|---|---|
| Vehicle | – | 1.12 ± 0.05 |
| 17-α -Estradiol | 0.01 | 1.16 ± 0.07 |
| 17-α -Estradiol | 0.1 | 1.43 ± 0.06 |
| 17-α -Estradiol | 0.5 | 1.52 ± 0.14 |
| 17-β -Estradiol | 0.001 | 1.25 ± 0.08 |
| 17-β -Estradiol | 0.01 | 1.62 ± 0.11 |
| 17-β -Estradiol | 0.1 | 1.50 ± 0.13 |

Signed and Sealed this

Sixth Day of January, 2004

JAMES E. ROGAN
*Director of the United States Patent and Trademark Office*